US009381175B2

(12) United States Patent
Kuo et al.

(10) Patent No.: US 9,381,175 B2
(45) Date of Patent: Jul. 5, 2016

(54) METHOD FOR TREATING CHIKUNGUNYA VIRUS INFECTION

(71) Applicants: Chung Yuan Christian University, Jongli, Taoyuan county (TW); National Defensive Medical Center, Taipei (TW)

(72) Inventors: Szu-Cheng Kuo, New Taipei (TW); Tzong-Yuan Wu, Panchiao (TW); Chang-Chi Lin, New Taipei (TW); Yu-Ming Wang, New Taipei (TW); Ying-Ju Chen, Yanpu Village (TW)

(73) Assignees: CHUNG YUAN CHRISTIAN UNIVERSITY, Jongli, Taoyuan County (TW); NATIONAL DEFENSIVE MEDICAL CENTER, Taipei (TW)

( * ) Notice: Subject to any disclaimer, the term of this patent is extended or adjusted under 35 U.S.C. 154(b) by 14 days.

(21) Appl. No.: 14/274,239

(22) Filed: May 28, 2014

(65) Prior Publication Data

US 2015/0342911 A1 Dec. 3, 2015

(51) Int. Cl.
*A61K 31/17* (2006.01)

(52) U.S. Cl.
CPC .................................... *A61K 31/17* (2013.01)

(58) Field of Classification Search
CPC .................................................. A61K 31/17
USPC ...................................................... 514/597
See application file for complete search history.

(56) References Cited

U.S. PATENT DOCUMENTS

2011/0065675 A1* 3/2011 Buchwald et al. ............ 514/150
2013/0189279 A1* 7/2013 Warter et al. .............. 424/159.1

OTHER PUBLICATIONS

Schwartz et al. "Biology and pathogenesis of chikungunya virus," Nature Reviews Microbiology, 2010, vol. 8, pp. 491-500.*

* cited by examiner

*Primary Examiner* — Shengjun Wang
(74) *Attorney, Agent, or Firm* — Muncy, Geissler, Olds & Lowe, P.C.

(57) ABSTRACT

Disclosed herein is a method for the treatment of an infection with, or disease caused by, Chikungunya virus in a subject. The method includes administering to the subject a therapeutically effective amount of suramin as the active agent.

5 Claims, 17 Drawing Sheets
(9 of 17 Drawing Sheet(s) Filed in Color)

METHOD FOR TREATING CHIKUNGUNYA VIRUS INFECTION

BACKGROUND OF THE INVENTION

1. Field of the Invention

The present disclosure relates to the treatment of infection. More particularly, the disclosed invention relates to the treatment of Chikungunya virus infection.

2. Description of Related Art

Chikungunya is a mosquito-borne virus mainly transmitted to vertebrates by *Aedes* mosquitoes such as *Aedes albopictus* and *Aedes aegypti* mosquitoes. Chikungunya virus (family Togaviridae, genus Alphavirus) has a positive sense single stranded RNA genome. Alphaviruses use receptor-mediated endocytic uptake and low pH-triggered membrane fusion to deliver their RNA genomes into the cytoplasm where productive replication occurs.

Chikungunya infection (also known as Chikungunya fever) was first identified in Tanzania and Uganda in 1953. Since then, re-emergences of Chikungunya infection outbreak have taken place in Africa, Southeast Asia, the Indian subcontinent and the Indian Ocean. In August 2007, the first outbreak in European continent was documented in Italy with 217 laboratory-confirmed cases. This outbreak was the first one reported in a temperate climate country. Currently, Chikungunya infection has been identified in more than 40 countries.

The symptoms of Chikungunya infection include sudden onset of fever, joint pain, muscle pain, headaches, nausea, vomiting, and nose and gum bleeding. Possible, but relatively rare complications include gastro-intestinal complications, cardiovascular decompensation, and meningo-ecephalitis. Averagely, the symptoms appear on 4 to 7 days after being bitten by an infected mosquito. While most patients usually recover after days to weeks, some may develop chronic arthritis. Death related to Chikungunya infection has been reported mainly in aged patients or patients with weakened immune systems.

Diagnostic tests are available but there is no antiviral or licensed vaccine. Accordingly, the treatment to Chikungunya infection is symptomatic including non-salicylate analgesics and non-steroid anti-inflammatory therapy.

In view of the foregoing, there exists a need in the art for providing a measure for treating and/or preventing Chikungunya infection.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a method for the treatment of an infection with, or a disease caused by, Chikungunya virus in a subject.

According to one embodiment of the present disclosure, the method comprises administering to the subject a therapeutically effective amount of suramin and a pharmaceutically acceptable excipient so as to inhibit the infection or replication of Chikungunya virus.

In various embodiments of the present disclosure, the subject can be a mouse or a human subject. According to various embodiments of the present disclosure, the suramin is injected intravenously or intramuscularly in 10% solution. The therapeutically effective amount per dose is about 1 to 2 g for adults, about 200 mg to 1 g for children, and about 10 to 200 mg for infants. The total dosage for a full course of treatment of suramin is about 5-20 g for adults, about 1 to 10 g for children and about 50 mg to 2 g.

According to some embodiments of the present disclosure, the infection or replication of Chikungunya virus is inhibited by blocking the membrane fusion of the Chikungunya virus. For example, the membrane fusion can be envelope protein-mediated membrane fusion.

In another aspect, the present disclosure is directed to a method for the suppression of membrane fusion of the Chikungunya virus in a host cell.

According to one embodiment of the present disclosure, the method comprises administering to the host cell an effective amount of suramin.

In some embodiments, the suppression of membrane fusion of the Chikungunya virus in a host cell is achieved by blocking envelope protein-mediated membrane fusion.

In certain embodiments, the host cell belongs to Sf21 cell line or BHK-21 cell line, and the effective amount is at least 27.5 µM. For example, the effective amount is about 27.5 µM to 1,750 µM; preferably, about 50 µM to 350 µM.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where:

FIG. 2 provides immunofluorescent photographs of Sf21 cells infected by the recombinant viruses according to Example 2 of the present disclosure; the bar represents 20 µm;

FIG. 7 and FIG. 8 illustrate the results of the cell fusion assay according to Example 5 of the present disclosure;

FIG. 9 is a line graph illustrating the result of in vitro antiviral assay according to Example 6 of the present disclosure;

DESCRIPTION

Figure 1:
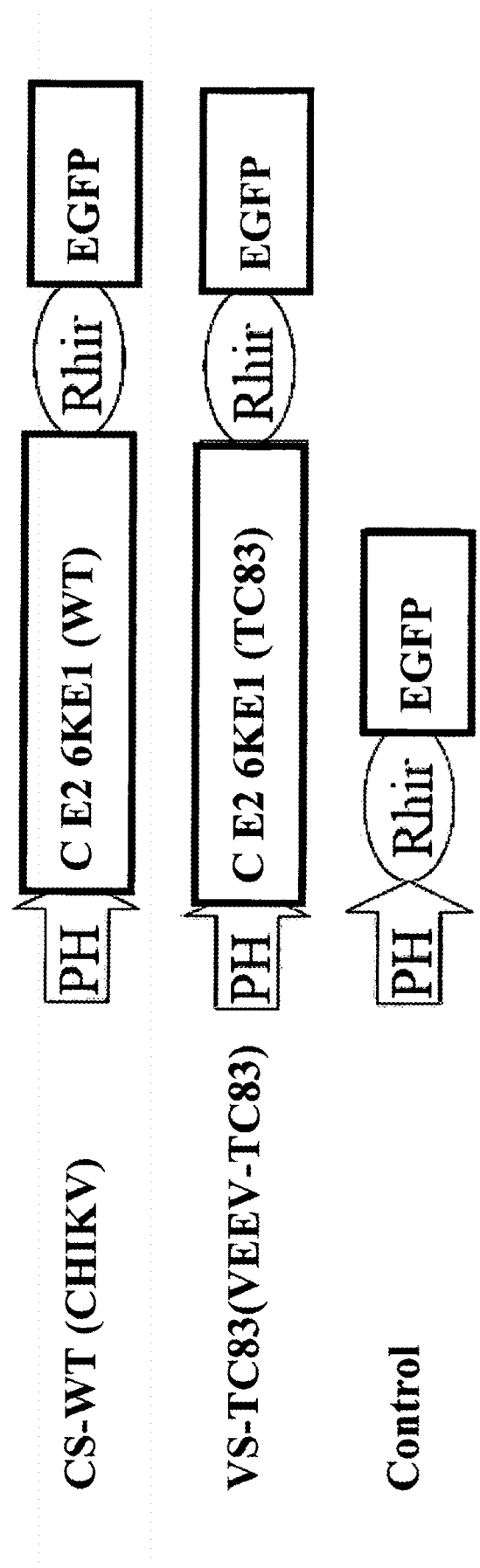
FIG. 1 is a schematic diagram illustrating the recombinant baculoviruses bearing a bi-cistronic system for co-expressing the full-length structural gene (26S) (including capsid (C), E2 glycoprotein (E2) and E1 glycoprotein (E1)) of wild-type CHIKV (CHIKV or CS-WT) or TC83 mutant of VEEV (VEEV-TC83 or VS-TC83) with EGFP according to Example 1 of the present disclosure; vector serves as control virus; abbreviations: PH, polyhedrin promoter; EGFP, enhanced green fluorescent protein gene; and Rhir, RhPV 5'-UTR IRES.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless defined otherwise, all technical and scientific terms used herein have the same meaning as commonly understood by one of the ordinary skill in the art to which this invention belongs.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art.

The terms "treatment" and "treating" are used herein to include preventative (e.g., prophylactic), curative, or palliative treatment that results in a desired pharmaceutical and/or physiological effect. Preferably, the effect is therapeutic in terms of partially or completely curing or preventing Chikungunya infection. Also, the terms "treatment" and "treating" as used herein refer to application or administration of suramin or pharmaceutical composition thereof to a subject, who has Chikungunya infection, a symptom of Chikungunya infection, a disease or disorder secondary to Chikungunya infection, or a predisposition toward Chikungunya infection, with the purpose to partially or completely alleviate, ameliorate, relieve, delay onset of, inhibit progression of, reduce severity of, and/or reduce incidence of one or more symptoms or features of Chikungunya infection. Generally, a "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable.

The term "therapeutically effective amount" as used herein refers to the quantity of a component (such as suramin) which is sufficient to yield a desired therapeutic response. A therapeutically effective amount is also one in which any toxic or detrimental effects of the compound or composition are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/kg).

As used herein, a "pharmaceutically acceptable excipient" is one that is suitable for use with the subjects without undue adverse side effects (such as toxicity, irritation, and allergic response) commensurate with a reasonable benefit/risk ratio. Also, each excipient must be "acceptable" in the sense of being compatible with the other ingredients of the pharmaceutical composition. The excipient can be in the form of a solid, semi-solid, or liquid diluent, cream or a capsule.

The term "subject" refers to a mammal including the human species that is treatable with suramin. The term "subject" is intended to refer to both the male and female gender unless one gender is specifically indicated.

The present invention is based, at least, on the finding that the suramin could be used as the sole active agent for the treatment of Chikungunya infection. Using a bicistronic baculovirus expression system capable of co-expressing EGFP and Chikungunya (CHIKV) structural protein in Sf21 cells, various compounds were screened for their ability un specifically inhibiting the membrane fusion of the Chikungunya virus. The screening result, as provided below, indicates that several candidate compounds (including heparin and dextran sulfate) can inhibit the membrane fusion of other Alphaviruses such as Venezuelan equine encephalitis virus, yet, they are not effective to inhibit the membrane fusion of Chikungunya viruses. However, suramin was found to block the membrane fusion of the Chikungunya viruses. Accordingly, suramin was subjected to in vitro assay. The result thereof establishes that suramin inhibits the infection and/or proliferation of the Chikungunya virus.

In one aspect, the present disclosure is directed to a method for the treatment of an infection with, or a disease caused by, Chikungunya virus in a subject.

According to one embodiment of the present disclosure, the method comprises administering to the subject a therapeutically effective amount of suramin and a pharmaceutically acceptable excipient, so as to inhibit the infection or replication of Chikungunya virus.

In certain embodiments, the subject is a mouse. In other embodiments, the subject is a human.

According to some embodiments of the present disclosure, the infection or replication of Chikungunya virus is inhibited by suppressing or blocking the membrane fusion of the Chikungunya virus. For example, the membrane fusion can be envelope protein-mediated membrane fusion.

In another aspect, the present disclosure is directed to a method for the suppression of membrane fusion of the Chikungunya virus in a host cell.

According to one embodiment of the present disclosure, the method comprises administering to the host cell an effective amount of suramin.

In some embodiments, the inhibition of the infection or replication of Chikungunya virus is achieved by blocking the membrane fusion of the Chikungunya virus. For example, the membrane fusion can be envelope protein-mediated membrane fusion.

In certain embodiments, the host cell belongs to Sf21 cell line or BHK-21 cell line, and the effective amount is at least 50 μM. For example, the effective amount of suramin can be 50, 55, 60, 65, 70, 75, 80, 85, 88, 90, 95, 100, 110, 120, 130, 140, 150, 160, 170, 175, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 μM.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

Example 1

Plasmid Construction, Recombinant Virus Production and Cell Infection

The backbones of baculovirus transfer vectors (pBac-Rhir-E) and pBac-CHIKV-26S-Rhir-E plasmid containing the full-length cDNA of the CHIKV 26S subgenomic RNA were constructed as previously described by Kuo et al. in "Cell-based analysis of Chikungunya virus membrane fusion using baculovirus-expression vectors" (J Virol Methods 2011, 175: 206-215). The full-length cDNA of the structural protein of the live-attenuated TC-83 strain of Venezuelan equine encephalitis virus (VEEV) was inserted into the baculovirus transfer vectors (pBac-Rhir-E) in the same manner to give the pBac-VEEV-TC83-26S-Rhir-E plasmid.

The IPBL-Sf21 (Sf21) cell line was cultured in Sf-900 II insect medium that contained 8% heat-inactivated fetal calf serum (FCS) at 27° C. For transfection, 1 μL of Cellfectin (Invitrogen, Carlsbad, Calif., USA) was added into the Sf21 cells, which were seeded at $2\times10^5$ cells per well in a 24-well plate. The cells were then co-transfected with 0.25 μg of the linearized viral DNA Bac-N-Blue (Invitrogen, Carlsbad, Calif., USA) and 0.8 μg of the plasmid. Recombinant viruses were collected from Sf21 cell cultures emitting green fluorescence under a fluorescence microscope (Nikon, Tokyo, Japan). Recombinant viruses (hereinafter, the vector, CS-WT and VS-TC83 viruses, FIG. 1) were purified by a series of three end-point dilutions. The viral titer was determined by end-point dilution and fluorescence detection in a 96-well plate and was calculated according to the 50% tissue culture infectious dose (TCID50) method. Sequences of all recombinant viruses were confirmed by viral DNA sequencing.

For virus infection, IPBL-Sf21 (Sf21) cells were seeded at $2\times10^6$ (6-well plate) or $10^5$ (96-well plate) cells per well in a 6-well plate and infected with recombinant baculoviruses at a multiplicity of infection (M.O.I.) of 1 in Sf-900 II insect medium, containing 8% fetal calf serum (FCS) at pH 6.4.

Example 2

Immunofluorescence Analysis

Infected cells from Example 1, above, were directly stained with rabbit anti-CHIKV E2 serum or mouse anti-VEEV serum at a dilution of 1:100 for 30 minutes at room temperature. After washing twice with cold PBS, cells were incubated with the secondary antibody, Alexa Fluor 594-conjugated goat anti-rabbit IgG or anti-mouse IgG (Invitrogen, Molecular Probes, Carlsbad, Calif., USA), at a dilution of 1:500 for 30 minutes at room temperature and then washed twice with cold PBS. The stained cells were recorded using an inverted fluorescence microscope (Model IX71, Olympus, Japan), red-channel for CHIKV E2 staining.

Figure 2:
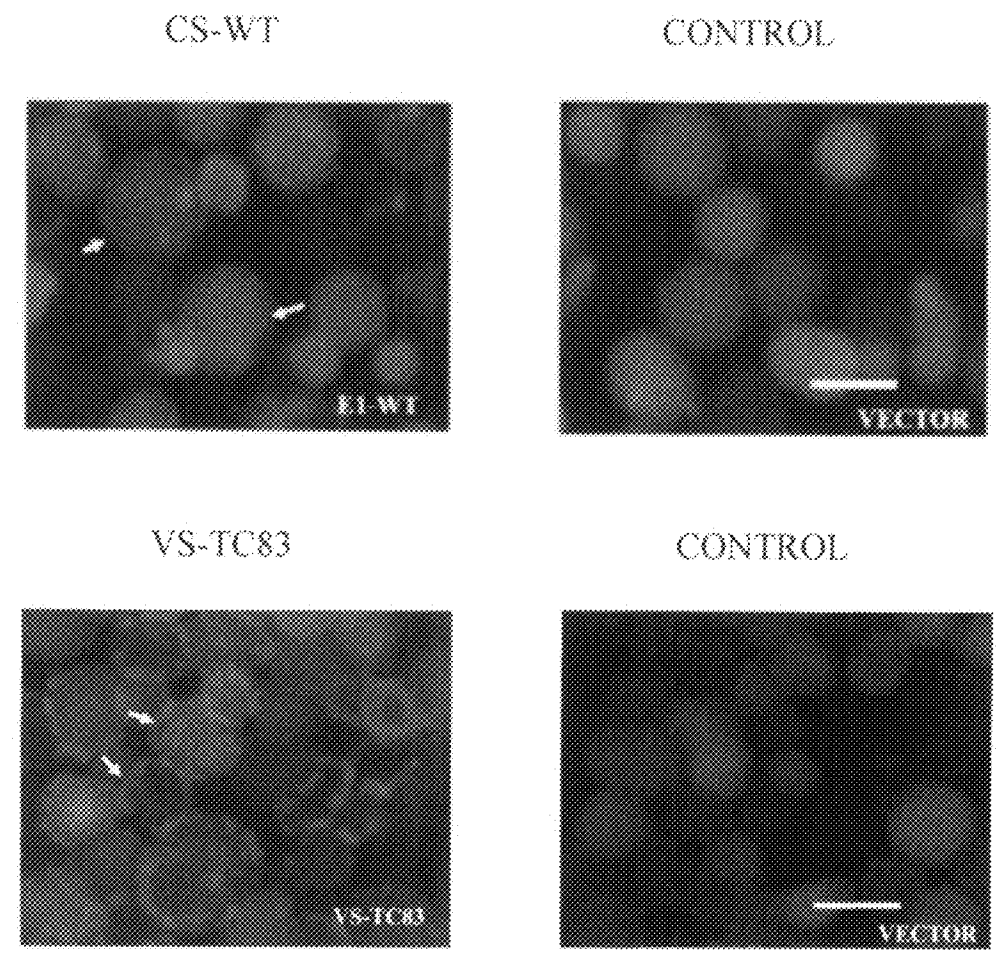

The green and red fluorescence on merged images of FIG. 2 respectively represent the infected-Sf21 cells expressing EGFP and viral glycoproteins signals (indicated by arrows). Red cells without the EGFP signal were dead cells. The red signals from viral glycoproteins present at the cell surface of the cells infected by either CS-WT (upper panel, FIG. 2) or VS-TC83 virus (lower panel, FIG. 2), indicated that viral glycoproteins of Alphavirus were displayed on the cell surface. In contrast, no red signal was detected in cells infected by control baculovirus (right panels, FIG. 2).

Example 3

Western Blot Analysis

For Western blot analysis of CHIKV viral protein, total proteins of Sf21 cells infected in Example 1 were harvested at 2 day post infection (dpi) and separated on 10% SDS-PAGE. After SDS-PAGE separation, proteins were electrotransferred onto a PVDF membrane (polyvinylidene difluoride; Millipore, Billerica, Mass., USA). The resulting membrane was blocked with Tris-buffered saline (TBS; 100 mM Tris (pH 7.4), 100 mM NaCl, and 0.1% Tween 20) containing 5% (v/v) non-fat dry milk at room temperature for 1 hour with gentle shaking Subsequently, the membrane was incubated with a 1:2000 dilution of anti-E2, anti-E1 or anti-CHIKV antibodies (for detecting capsid) in TBS with 5% (v/v) non-fat dry milk at 4° C. overnight. Unbound antibodies were removed by washing three times for 5 minutes each time with TBS buffer at room temperature with shaking. The membrane was then incubated with a 1:2500 dilution of peroxidase-conjugated goat anti-Rabbit IgG (Jackson ImmunoResearch Laboratories, Inc., Pennsylvania, Calif., USA) for 1 hour at room temperature. HRP on the membrane was detected by the LumiFast Plus Chemiluminescence Detection Kit (T-Pro Biotechnology, Taiwan, R.O.C) following the protocol provided by the manufacturer. The UVP AutoChemi Image System was used for capturing and processing the images.

Figures 3, 4:
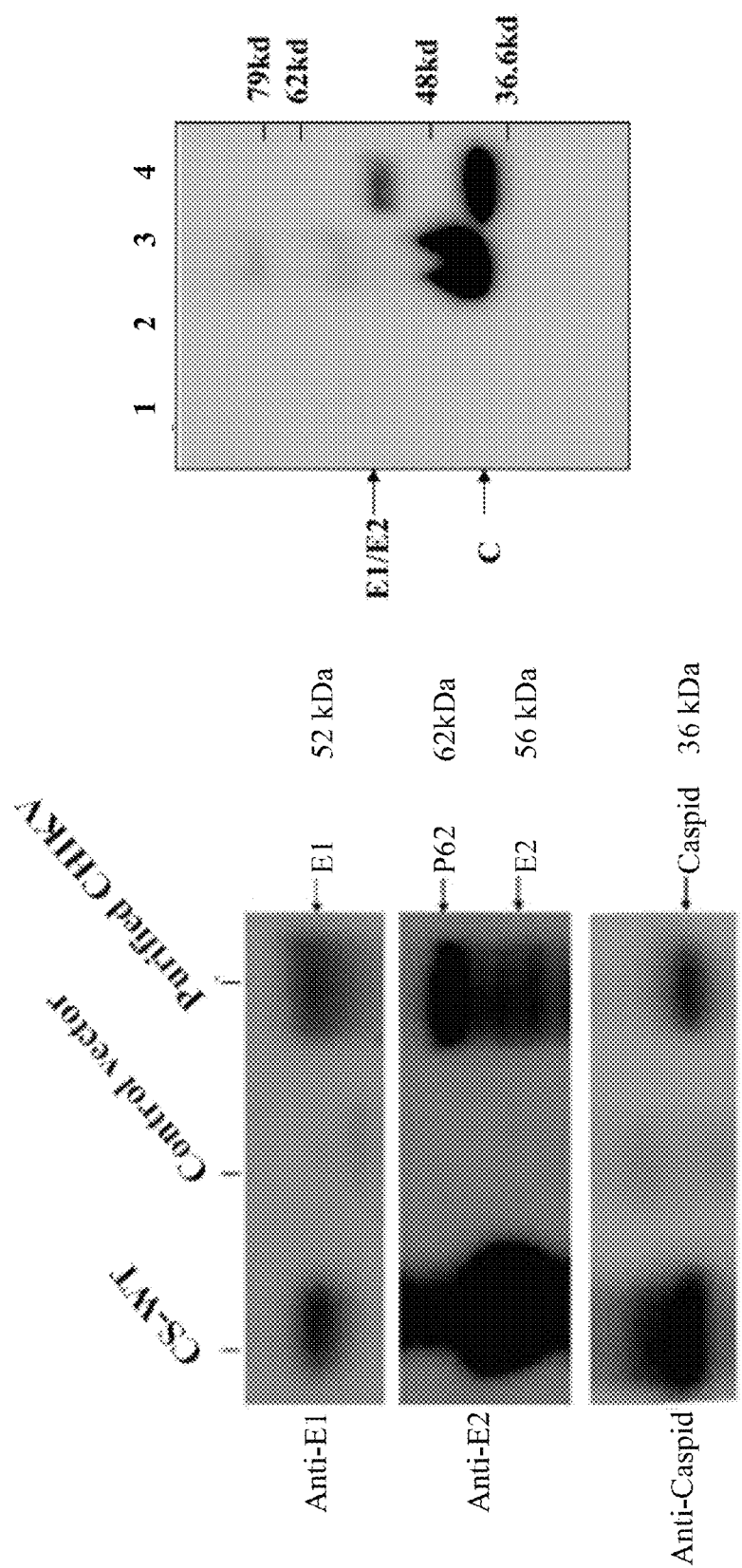
FIG. 3 and FIG. 4 provide photographs of Western blot analysis representing the results according to Example 3 of the present disclosure.

Protein bands migrating to the 52, 56 and 36 kDa gel positions corresponding to CHIKV E1, E2 and C were detected in cells infected by CS-WT viruses (upper panel, FIG. 3) and purified CHIKV, but not in those infected by the control virus (Lane 2, FIG. 3). These results indicate that Sf21 cells infected by CS-WT can express the E1, E2 and C proteins of CHIKV.

Viral proteins of VEEV-TC83 were collected at 2 dpi and treated using the protocol described above except that mouse anti-VEEV serum was used. The results, as illustrated in FIG. 4, indicate that no viral structural proteins were detected in the uninfected Sf21 cell (lane 1, negative control) and the Sf21 cells infected by control virus (lane 2, positive control). On the other hand, the viral capsid protein was detected in Sf21 cells infected by VS-TC83 virus (lane 3, FIG. 4), whereas both the viral capsid protein and the viral E1/E2 protein were detected in BHK-21 cells infected by VEEV-TC83 virus (lane 4, FIG. 4).

Example 4

Recombinant Virus-Induced Cell Fusion

Figure 5:
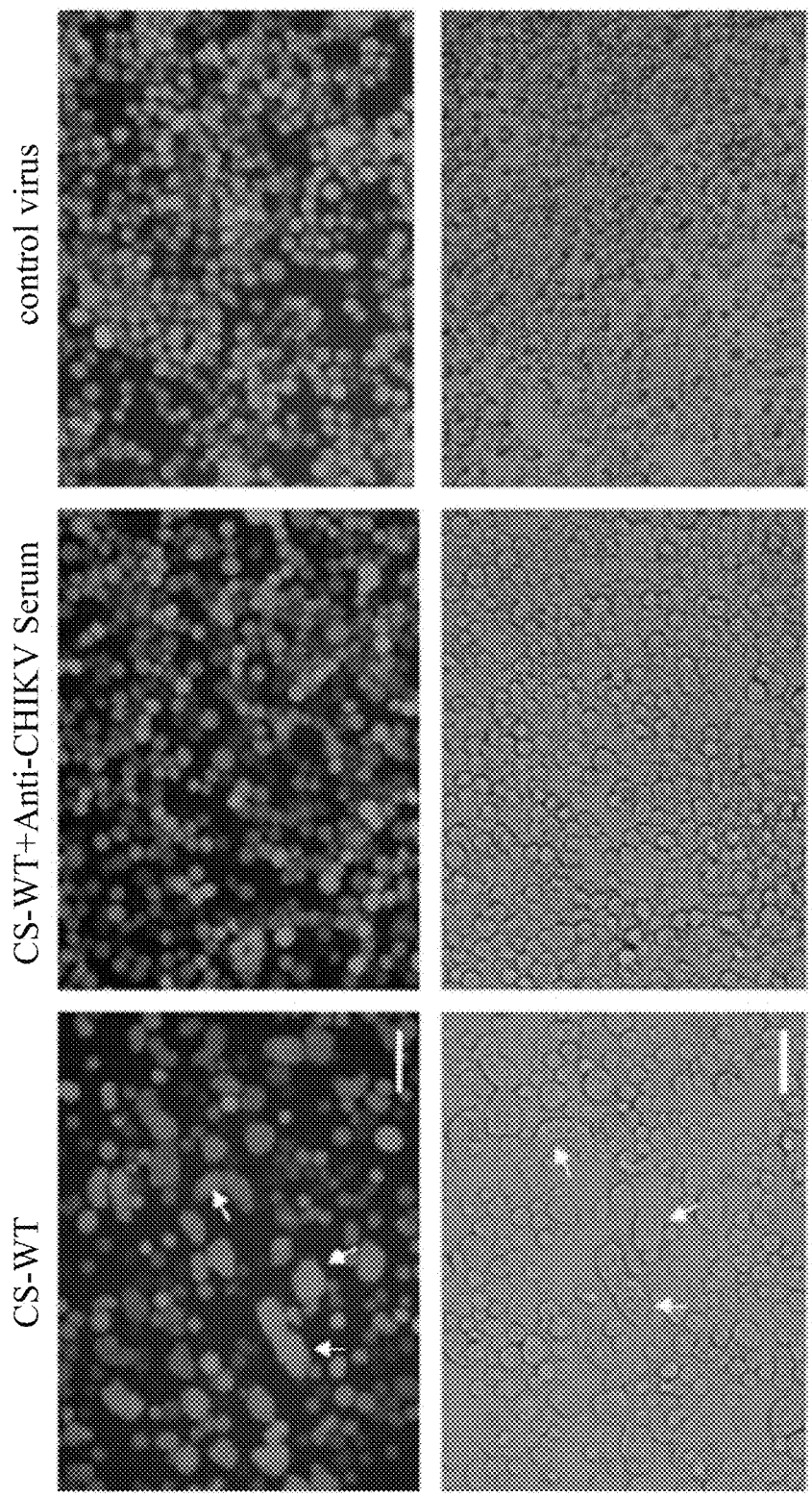
FIG. 5 and FIG. 6 provide fluorescent photographs of Sf21 cells infected by the recombinant viruses and treated according to Example 4 of the present disclosure; the bar represents 25 µm.

Sf21 cells infected by CS-WT virus with or without further treatment of anti-CHIKV serum (1:200), and infected by control virus were examined under a fluorescence microscope with a FITC channel (upper panel, FIG. 5) or a bright field (lower panel, FIG. 5), and images of the same field were taken. In the control group, no cell fusion was observed in Sf21 cells infected by control virus (right panel, FIG. 5). Cell fusion was observed in Sf21 cells infected with CS-WT viruses and without the anti-CHIKV serum treatment (left panel, FIG. 5; polykaryotic cells were indicated by arrows). The treatment with anti-CHIKV serum effectively inhibited the cell fusion induced by the infection of CS-WT virus (middle panel, FIG. 5).

Figure 6:
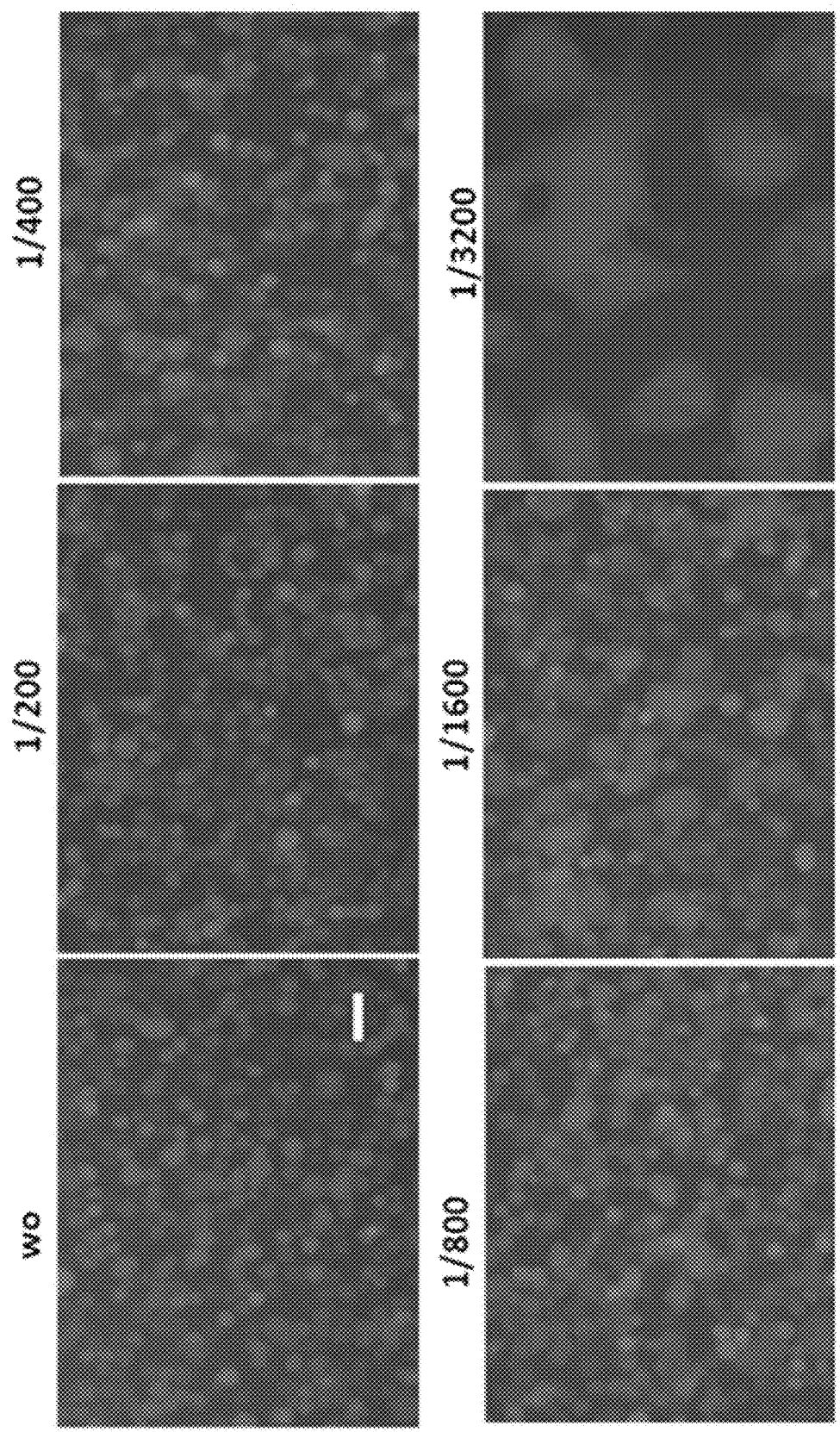

To investigate the dose-dependency of the inhibition of cell fusion by antiserum, Sf21 cells were infected with CS-WT viruses at multiplicity of infection M.O.I. of 1 in Sf-900 II containing 8% FCS. At 1 dpi, cells were incubated with different dilutions (0 (wo), 1:200, 1:400, 1:800, 1:1600 and 1:3200) of rabbit anti-whole CHIKV serum in growth medium for 1 hour at 27° C. Thereafter, the medium was replaced with medium with Sf-900 II (pH 5.8) containing 2% FCS, 0.1 mg/ml cholesterol and a corresponding diluted serum. The samples were then examined and imaged under an inverted fluorescence microscope (IX71; Olympus) at 2 dpi. The results as provided in FIG. 6 indicate that the inhibitory effect of the antiserum on cell fusion increased as the concentration of the antiserum increased.

Example 5

Effect of Selected Polysaccharides on Recombinant Virus-Induced Cell Fusion

Sf21 cells were infected with the recombinant baculoviruses according to the protocol described in Example 1, above. At 2 dpi, infected Sf21 cells were pretreated with growth medium containing polysaccharides of chrondroitin sulfate (1 mg/mL), chitosan (2 μg/mL), dextran sulfate (1 mg/mL), heparin (1 mg/mL), hyaluronic acid (1 mg/mL), mannan (1 mg/mL) and incubated for 1 hour. The culture medium was then replaced with Sf-900 II SFM containing a specified polysaccharide of the above-prescribed concentration, 0.1 mg cholesterol/mL and 2% FCS (pH 5.8) and incubated for 2 hours. Subsequently, cell fusion formation was examined under a fluorescence microscope; at least 100 nuclei per field were counted at a 200× magnification. The fusion index was calculated by dividing the number of multiple nuclei cells with the number of EGFP-positive cells, and the results are summarized in FIG. 7.

Figure 7:
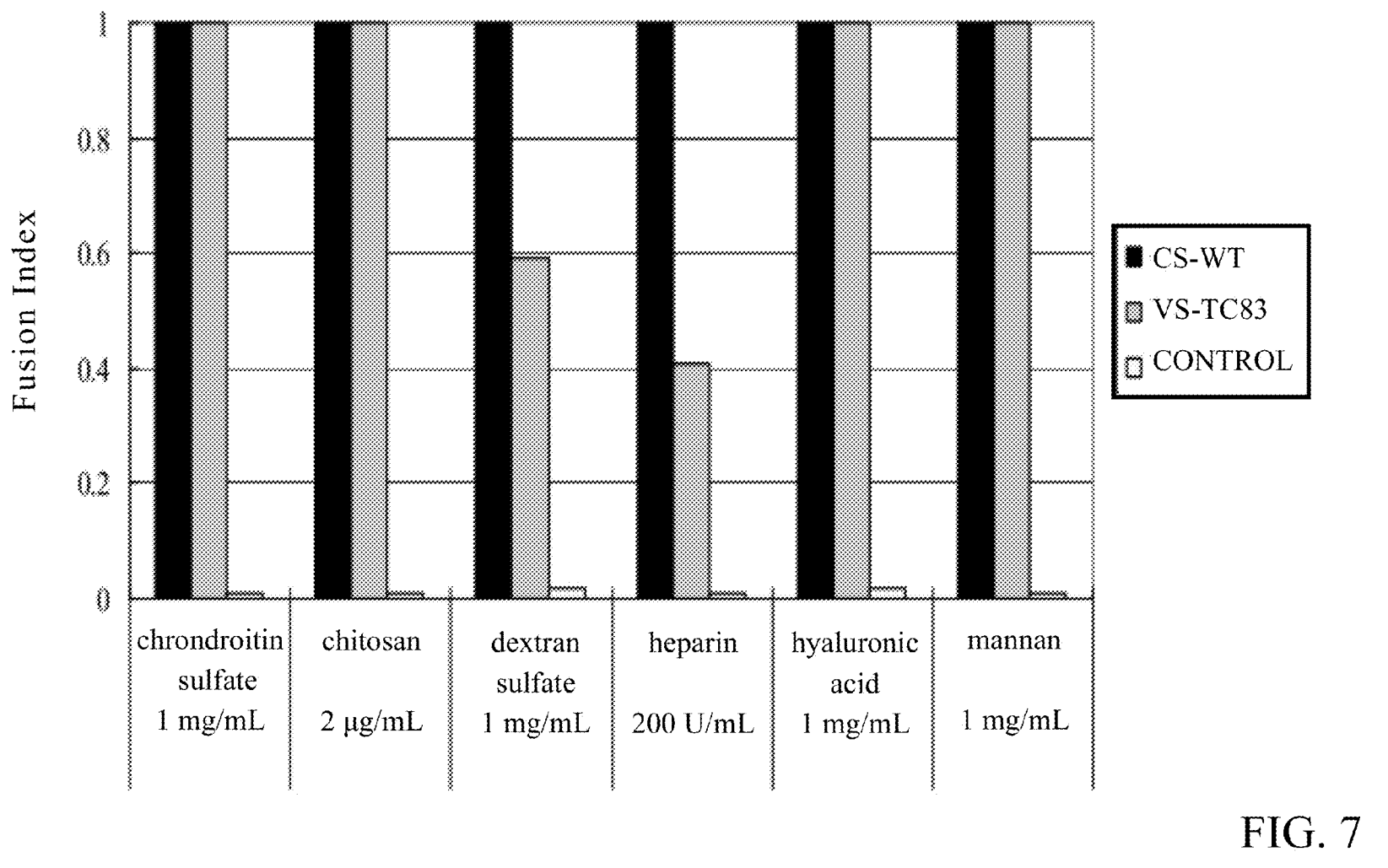

As can be seen in FIG. 7, none of the tested polysaccharides at the prescribed dosage can inhibit the fusion of Sf21 cells infected with CS-WT viruses (CHIKV). On the other hand, two (i.e., dextran sulfate and heparin) out of six tested compound substantially inhibit the fusion of Sf21 cells infected with vAc-VS-TC83-26S-Rhir-E (VS-TC83) viruses. In the control group, only marginal cell fusion was observed in Sf2 cells infected by control virus (control).

Various concentrations of mannan, heparin and dextran sulfate were added into the medium of the Sf21 cells infected with either CS-WT (CHIKV) viruses or VS-TC83 (VEEV-TC83) viruses according to the protocol described above. The results were expressed as fusion index and summarized in FIG. 8.

Figure 8:
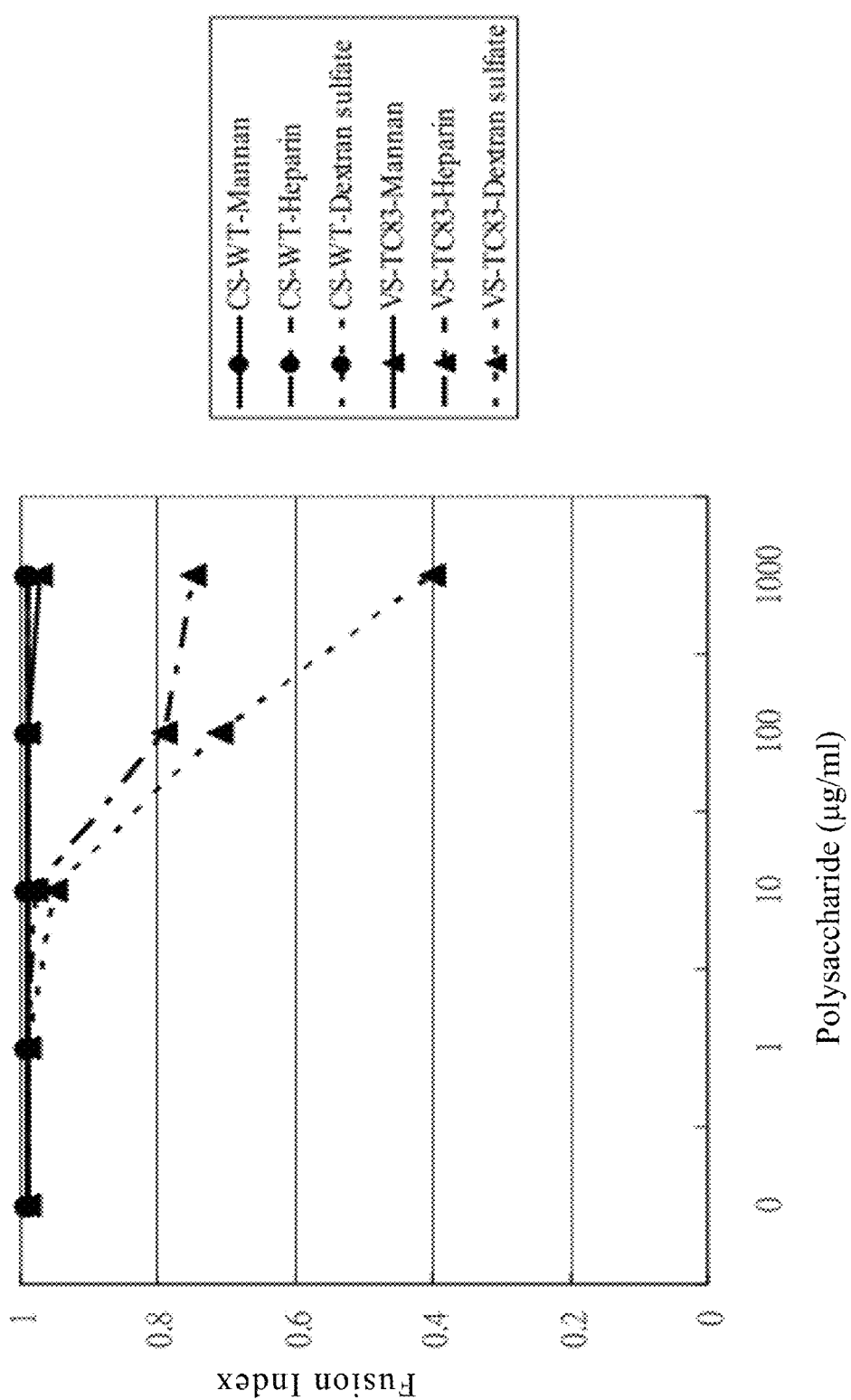

As indicated in FIG. 8, heparin and dextran sulfate (1, 10, 100 and 1000 μg/ml) respectively inhibit the cell fusion induced by VS-TC83 virus in a dose-dependent manner. However, none of the tested compounds inhibits the cell fusion induced by CS-WT virus at the specified doses.

Example 6

Effect of Selected Polysaccharides on Inhibition of VEEV-TC83 Infection

Figure 9:
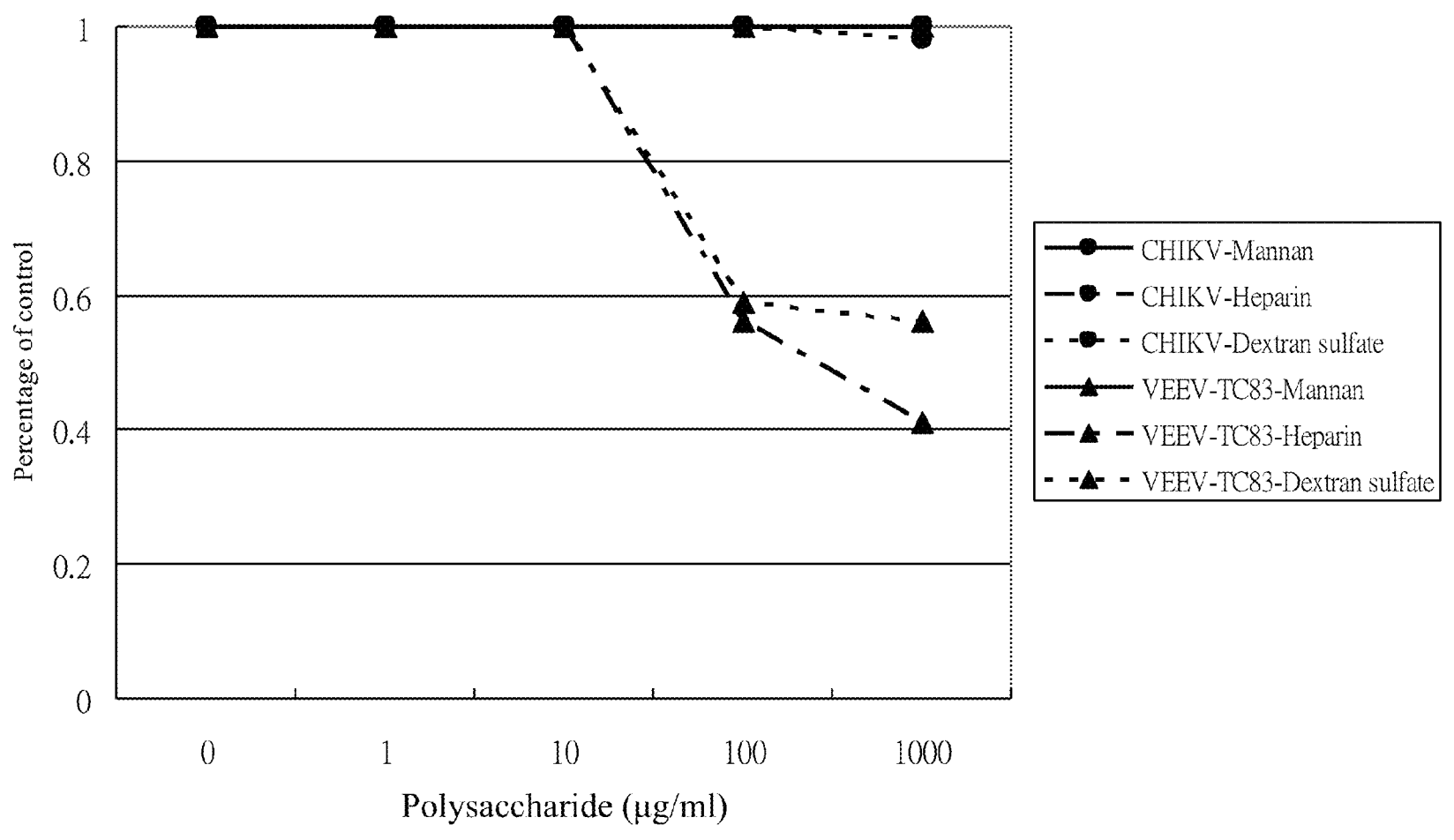

Another cell line, BHK-21 cells was also used to test the antiviral effect of polysaccharides on either CHIKV or VEEV-TC83 infection. Briefly, BHK-21 cells were seeded on 6-well plate. Viruses were incubated with prescribed concentrations of mannan, dextran sulfate and heparin for 30 minutes on ice, and then the preparations were used to infect BHK-21 cells for 30 minutes on ice followed by washing with the growth medium before being transferred to 37° C. for 24 hours incubation. The result of plaque reduction assay were then examined and calculated as described above, and the results are summarized in FIG. 9.

Gel electrophoresis was also performed to elucidate the effect of polysaccharides on the production of viral capsid protein. Briefly, BHK-21 cells were infected by CHIKV or VEEV-TC83 viruses pretreated with mannan (0.32 mg/ml), dextran sulfate (0.625 mg/ml) or heparin (1 mg/ml) according to the protocol set forth above. At 1 dpi, total proteins separated on 10% SDS-PAGE. Viral capsid proteins were detected by Western blot analysis using anti-VEEV serum or anti-CHIKV serum. Membranes were stripped and re-probing with tubulin antibody serves as control. Results are presented in FIG. 10.

Figure 10:
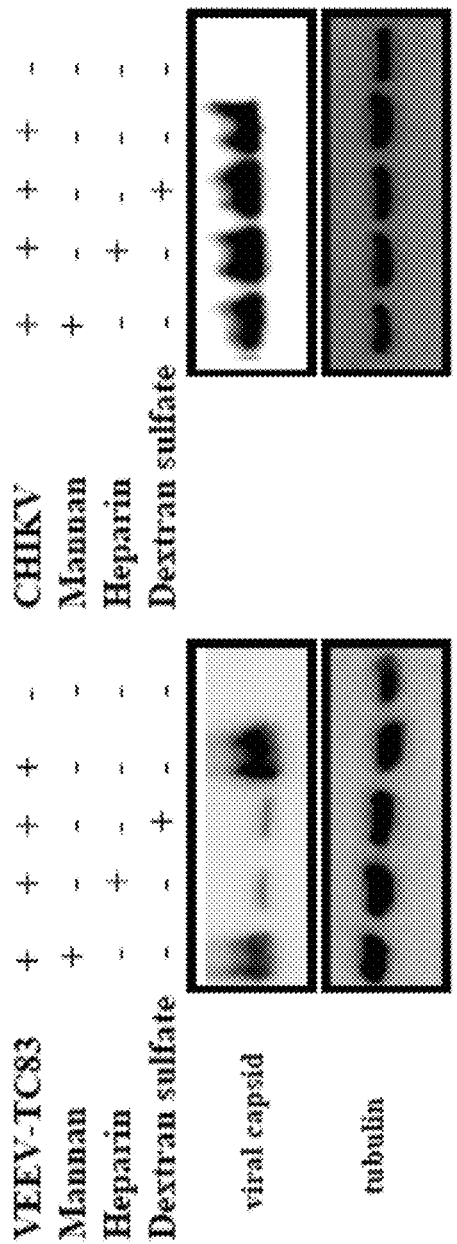
FIG. 10 provides photographs of Western blot analysis representing the results according to Example 6 of the present disclosure.

As could be seen in FIG. 10, none of the tested compounds was effective in inhibiting CHIKV infection and heparin and dextran sulfate elicited dose-dependent inhibition of VEEV-TC83 infection.

Example 7

Effect of Suramin on Recombinant Virus-Induced Cell Fusion

In addition to the polysaccharides identified in Example 6, above, the recombinant viruses prepared in Example 1, above, was used as a platform for systematic screening of FDA-approved drug library (L1300, Selleckchem), antiviral agents and synthetic peptides to identify possible candidate (s) capable of inhibiting cell fusion induced by CS-WT infection. Most of the tested compounds, including several known antiviral agents such as arbidol, silymarin, carrageenan, ezetimibe and synthetic peptides, failed to inhibit the cell fusion of the infected cells (data not shown). During the primary screening, only one compound, suramin, substantially inhibited the cell fusion of the infected Sf21 cells.

Specifically, $10^5$ Sf21 cells were seeded in a 96-wells plate and infected with CS-WT viruses at an M.O.I. of 1. At 1 dpi, the medium was replaced with Sf-900 II SFM (pH 6.8 and 2% FCS) to prevent the cell fusion. At 2 dpi, the medium was replaced with Sf-900 II SFM (pH 5.8, 0.1 mg/mL cholesterol and 2% FCS) containing 5 mg/mL chondroitin sulfate or 5 mg/mL (350 µM) suramin, and then incubated for 2 hours. Cell fusion was examined and photographed using an inverted fluorescence microscope (Olympus Model IX71, Tokyo, Japan); results are provided in FIG. 11.

Figure 11:
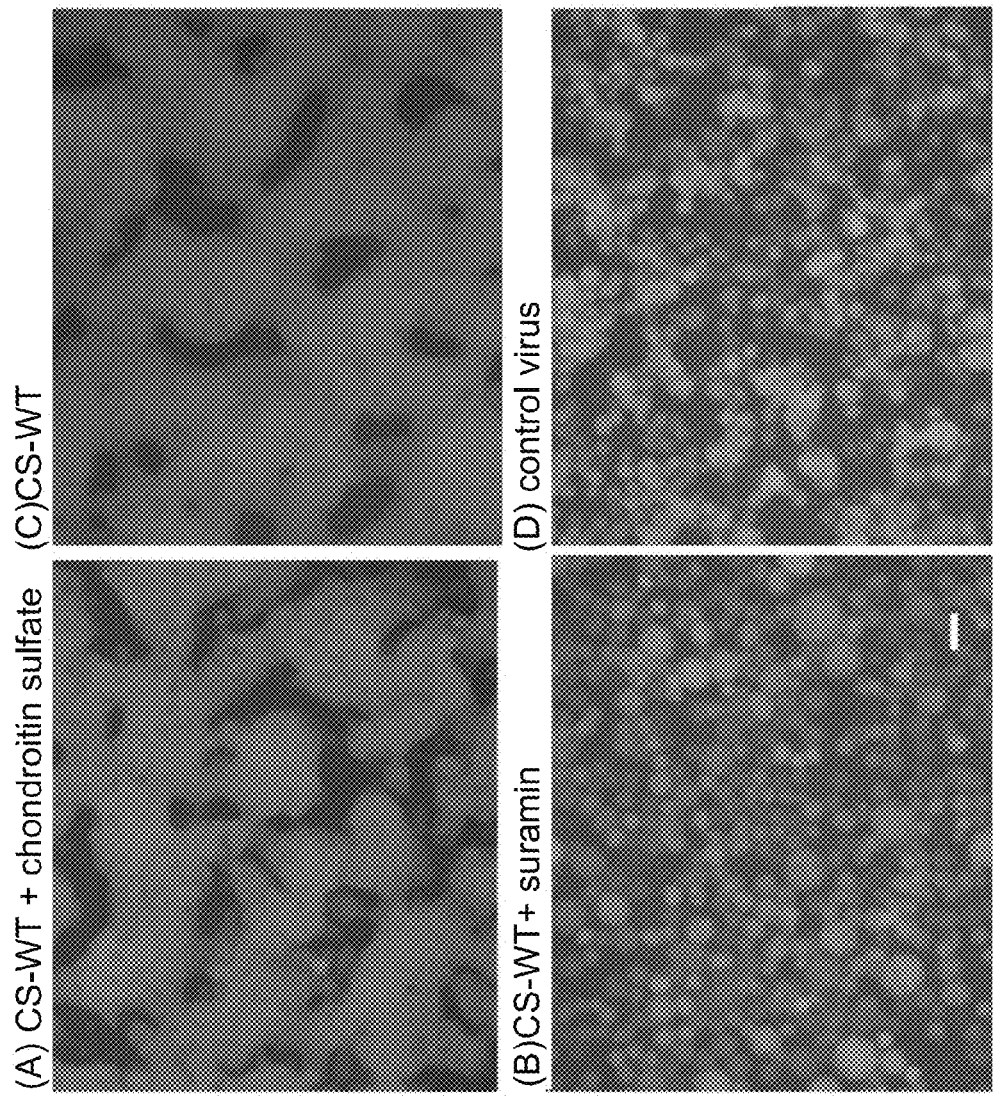
FIG. 11 provides fluorescent photographs of Sf21 cells infected by the recombinant viruses and treated according to Example 7 of the present disclosure; the bar represents 20 μm.

As compared to the control virus (panel (D), FIG. 11), CS-WT induced the Sf21 cell fusion (panel (C), FIG. 11). While chondroitin sulfate did not substantially inhibit the cell fusion (panel (A), FIG. 11), suramin remarkably inhibited the cell fusion in the infected Sf21 cells (panel (B), FIG. 11).

Figure 12:
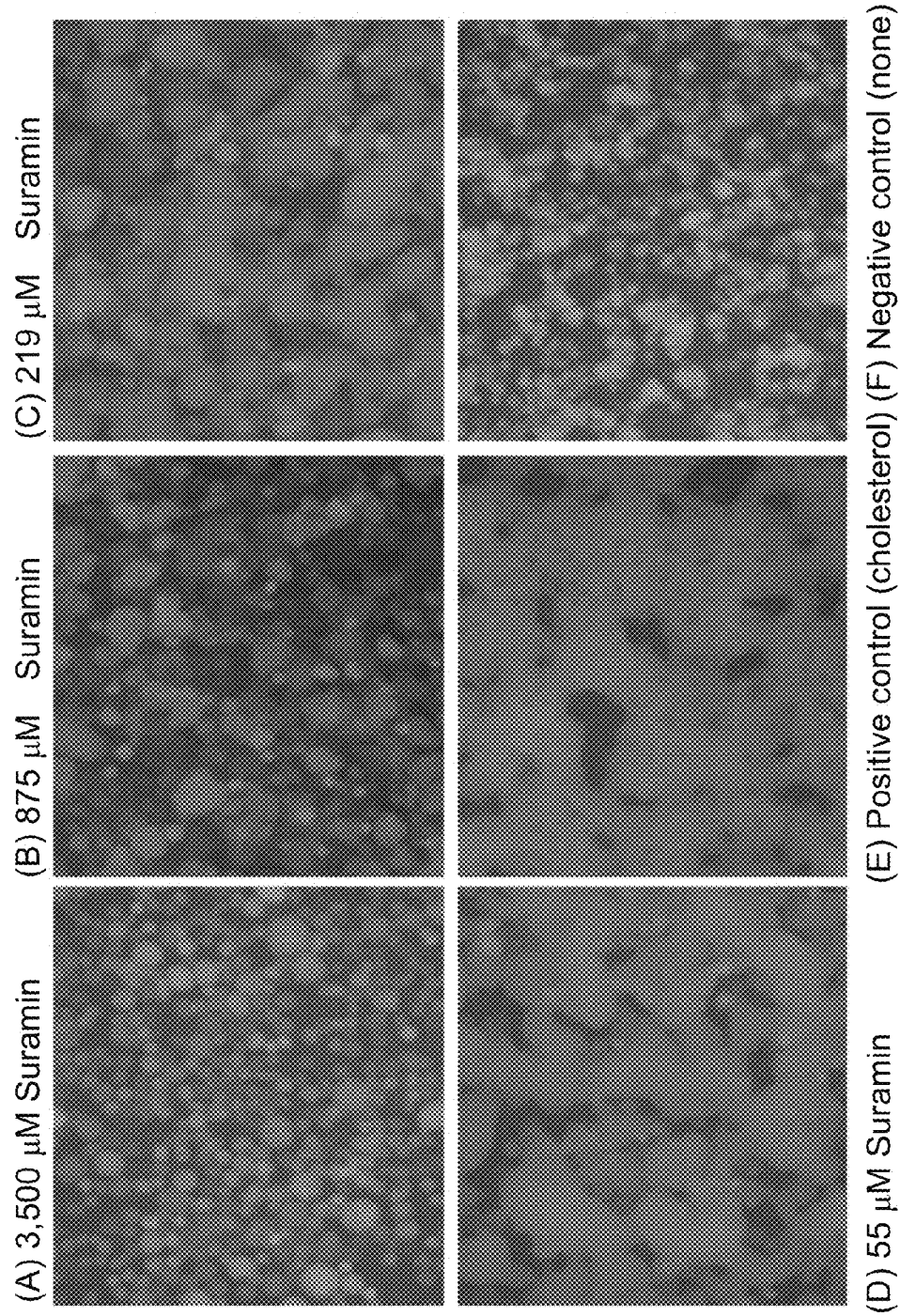
FIG. 12 provides fluorescent photographs of Sf21 cells infected by the recombinant viruses and treated according to Example 8 of the present disclosure.

Dose-dependent inhibition of suramin against cell fusion of infected Sf21 cells was observed by administering 3,500 µM, 875 µM, 219 µM or 55 µM suramin using the protocol set forth above. Cell fusion was examined and photographed using the inverted fluorescence microscope; results are provided in FIG. 12.

Figure 13:
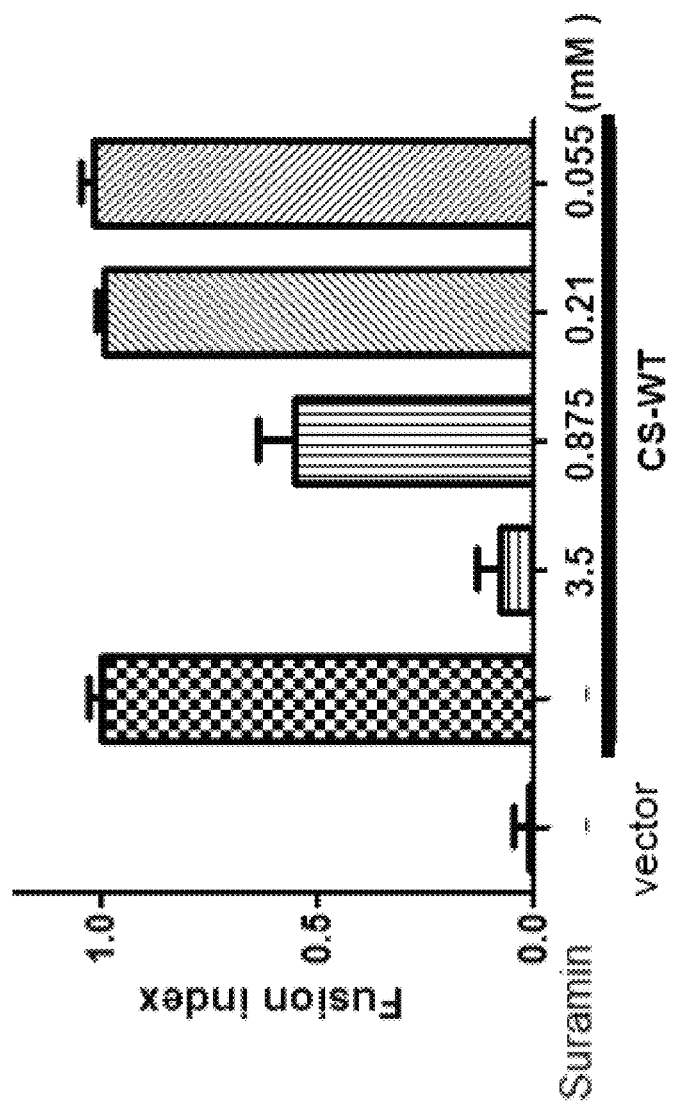
FIG. 13 is a histogram illustrating the result of the cell fusion assay according to Example 7 of the present disclosure.

Inhibition efficacy was also expressed as "fusion index," in which a lower fusion index indicates a better inhibitory efficacy. The results, as illustrated in FIG. 13, indicate that in the specified dose range, the inhibitory efficacy of suramin increases as the concentration of suramin increases, while the inhibitory effect solicited by 55 µM suramin was minimal.

Example 8

Effect of Suramin on CHIKV Structural Protein Production

BHK-21 cells were infected with CHIKV to investigate whether suramin inhibits CHIKV viral proteins expression, so as to further validate whether the above-mentioned screening system of baculovirus/insect cell can be used to screen candidate compounds capable of inhibiting CHIKV infection. Briefly, BHK-21 cells were seeded into a 12-well plate. 1 mL of DMEM containing 2% FCS, 10,000 plaque-forming units (PFU) CHIKV, and suramin of prescribed concentration was added into each well. For time-of-addition assay, final concentration of 350 µM suramin was added at 0, 1, 2, 3, or 4 hours after infection, and the total incubation time was 20 hours. After incubation, the cells were lysed with 500 µL of 1× sample buffer. Total protein was separated on SDS-PAGE (20 µL per well). Western blotting was conducted by staining with rabbit anti-CHIKV E2 serum (1:1000), Rabbit anti-whole CHIKV serum (1:2000) or anti-actin MAb (A4700, Sigma; 1:500).

Figure 14:
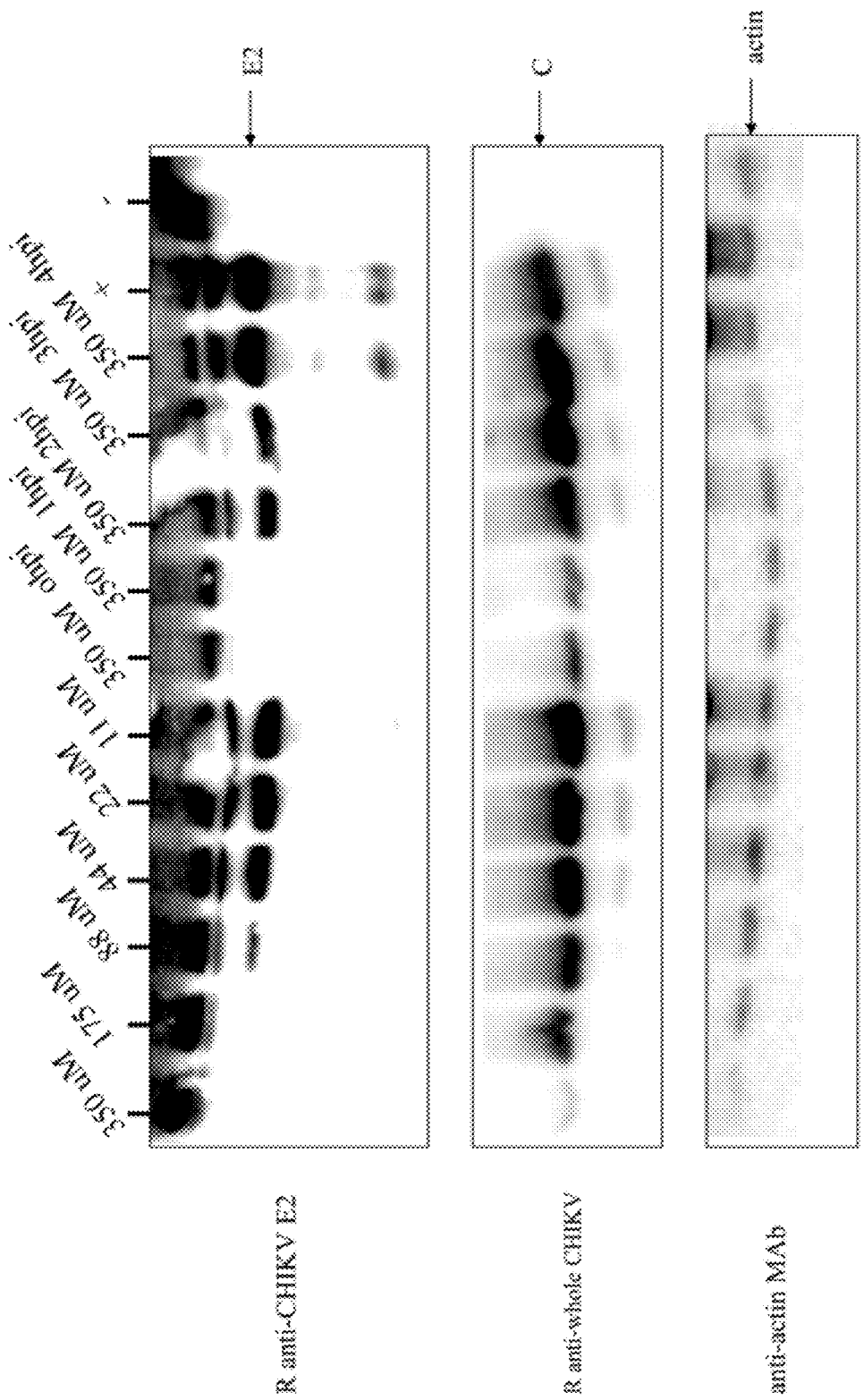
FIG. 14 is a photograph of Western blot analysis representing the result according to Example 9 of the present disclosure.

The results of Western blot analysis, as provided in FIG. 14, indicate the dose-dependency of the inhibitory effect of suramin on the production of the structural proteins of CHIKV. Similar to the results observed in FIGS. 12 and 13, a suramin concentration of 44 µM exhibited only marginal inhibitory effect. The results of time-of-addition assay reveal that the inhibition activity of suramin takes place in the early stage (0-2 hours post infection) in the virus life cycle.

Example 9

In Vitro Inhibition of Suramin on CHIKV Infection

BHK-21 cells were infected with CHIKV at an M.O.I. of 1 in the presence of 175 µM (2.5 mg/mL) suramin (group A) or 12.5 µg/ml ribavirin (group B); for positive control, cells were infected with CHIKV without additional treatment (group C); cells that were not infected with CHIKV were used as the negative control (group D). After incubation for 20 hours, cells were permeabilized with acetone and stained with rabbit anti-CHIKV E2 serum at a dilution of 1:100 for 30 minutes at room temperature. After washing with cold PBS twice, cells were incubated with a secondary antibody, Alexa Fluor 594-conjugated goat anti-rabbit IgG (Invitrogen, Molecular Probes, Carlsbad, Calif., USA), at a dilution of 1:500 for 30 minutes at room temperature and then washed with cold PBS twice. The stained cells were imagined using an inverted fluorescence microscope (Model IX71, Olympus, Japan), red-channel for CHIKV E2 staining.

Figure 15:
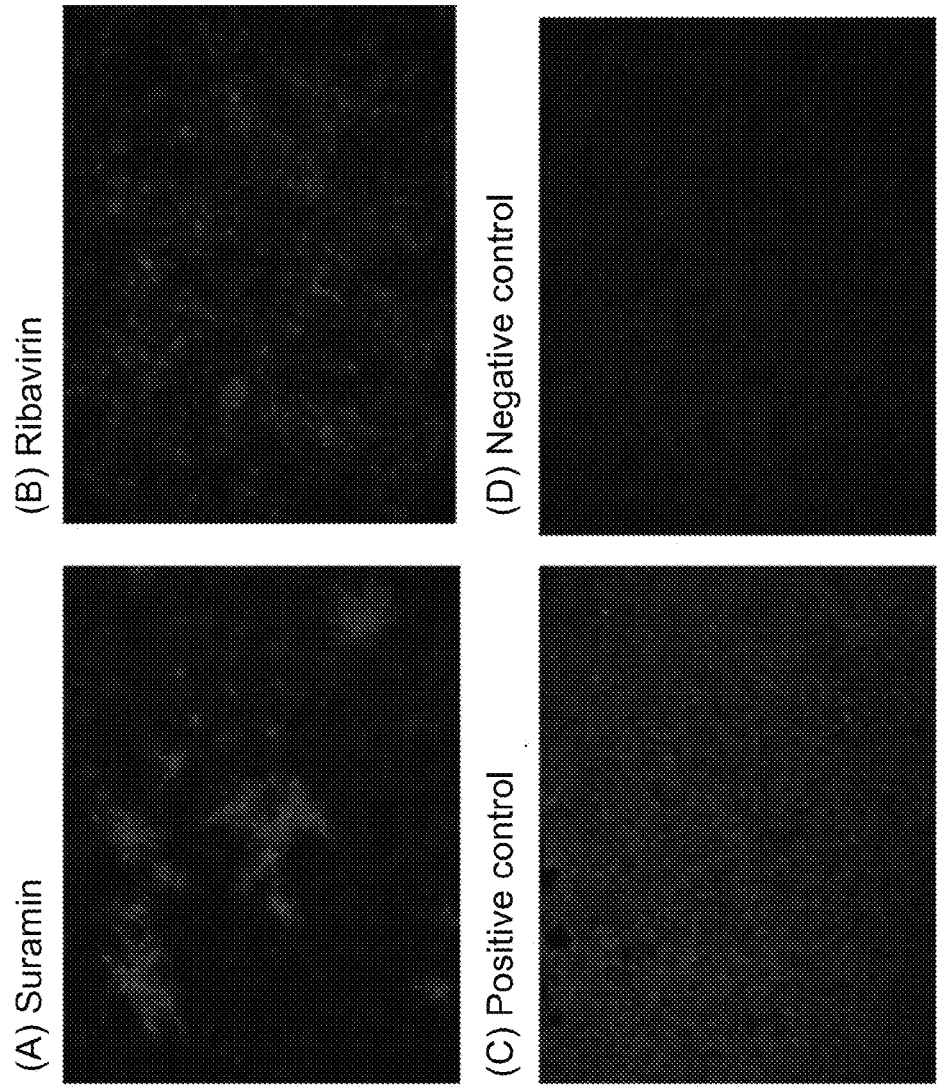
FIGS. 15 to 17 provide immunofluorescent photographs of BHK-21 cells infected by CHIKV viruses and treated according to Example 9 of the present disclosure.

The results, as provided in FIG. 15, indicate that the addition of suramin inhibit CHIKV infection in vitro (panel A), and the inhibition efficacy of suramin is higher than that of ribavirin (panel B).

To elucidate the dose-dependency of suramin in inhibiting in vitro CHIKV infection, BHK-21 cells were seeded into a 96-well plate; 100 µL of DMEM (containing 2% FCS, 2,000 PFU of CHIKV and suramin of prescribed concentration) was added into each well. After 20 hours of incubation, immunofluorescence assay was performed according to the protocol set forth above in this example.

Figure 16:
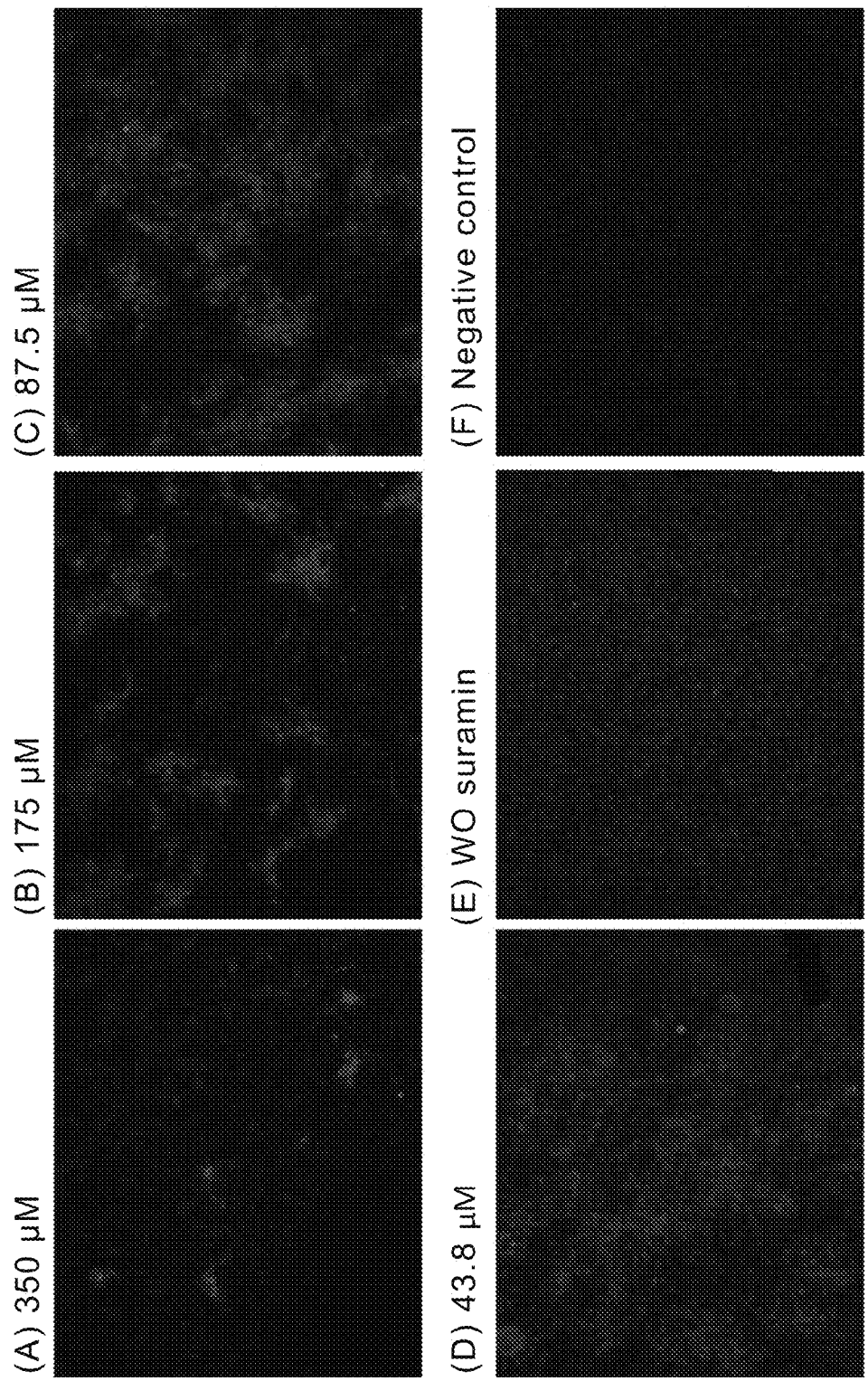

The results provided in FIG. 16 illustrate that the in vitro inhibition efficacy of suramin against CHIKV increases as the concentration of suramin increases. At a dose of less than 44 µM suramin exhibits marginal inhibitory effect in vitro (panel D, FIG. 16).

Figure 17:
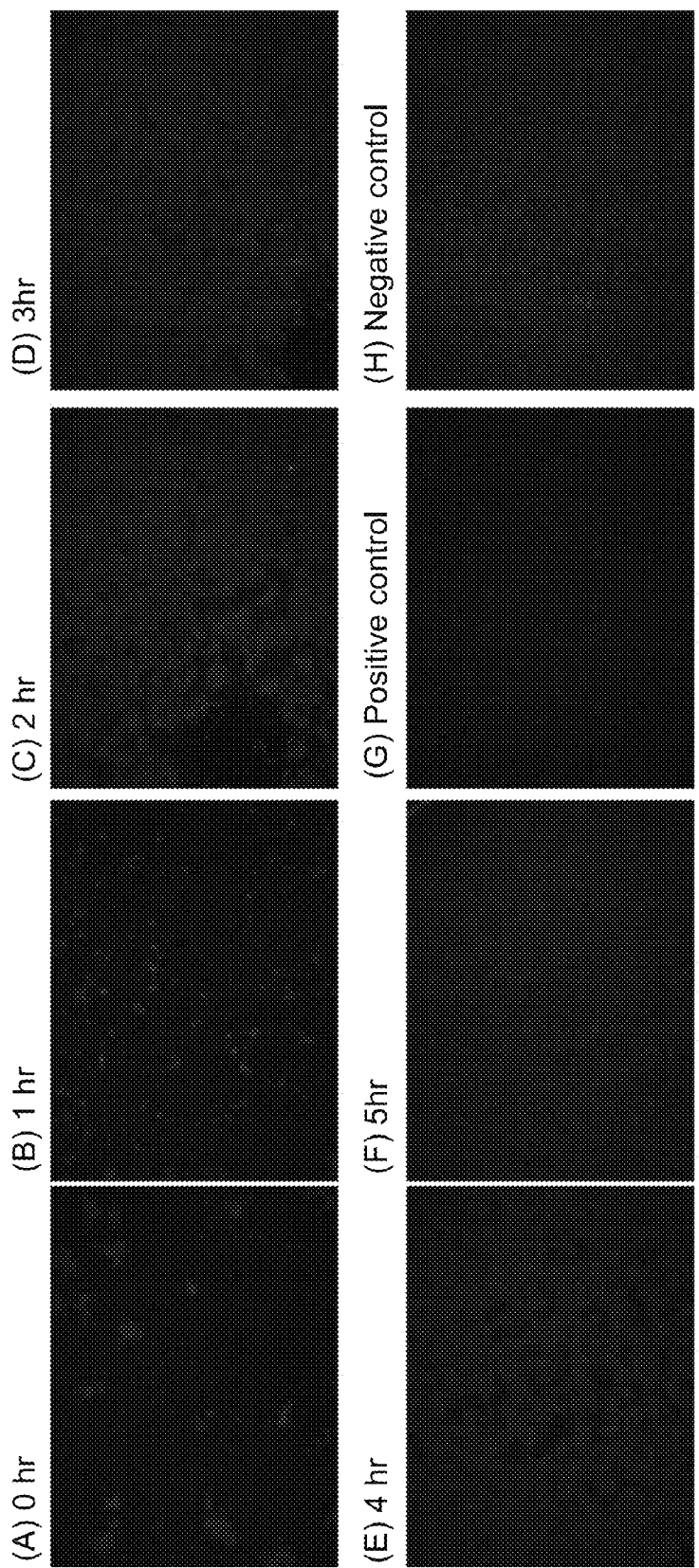

For time-of-addition assay, BHK-21 cells were seeded into a 96-well plate. 50 µL of DMEM containing 2% FCS and 2,000 PFU CHIKV was added into each well. 5 mg/mL (350 µM) suramin was added into each cell at a prescribed time after infection, and the mixture was incubated for 20 hours. Thereafter, immunofluorescence assay was performed following the above-mentioned protocol, and the results were provided in FIG. 17. The results of time-of-addition assay reveal that the inhibition activity of suramin takes place in the early stage (0-2 hours post infection; panels (A) to (C), FIG. 17) in the virus life cycle, while the addition of suramin at a later stage exhibits almost no inhibitory effect (panels (D) to (F); FIG. 17).

Example 10

Cytotoxicity Assay and Cell Protection Assay of Suramin Against CHIKV Infection $10^5$ BHK-21 cells per well of 96-well plate were cultured with 2% FCS DMEM. For cykotoxicity assay, cells were cultured in the presence or absence of drug at various concentrations in duplication for 2 days. For cell protection assay, cells were infected with CHIKV at moi of 0.05 in the presence or absence of drugs at various concentrations in duplication for 2 days. Cells were then stained with 0.1% crystal violet solution to observe clearance of the cell monolayer caused by the cytotoxic or cytopathic effect. Crystal violet was quantified by optical density (OD) 540.

Figure 18:
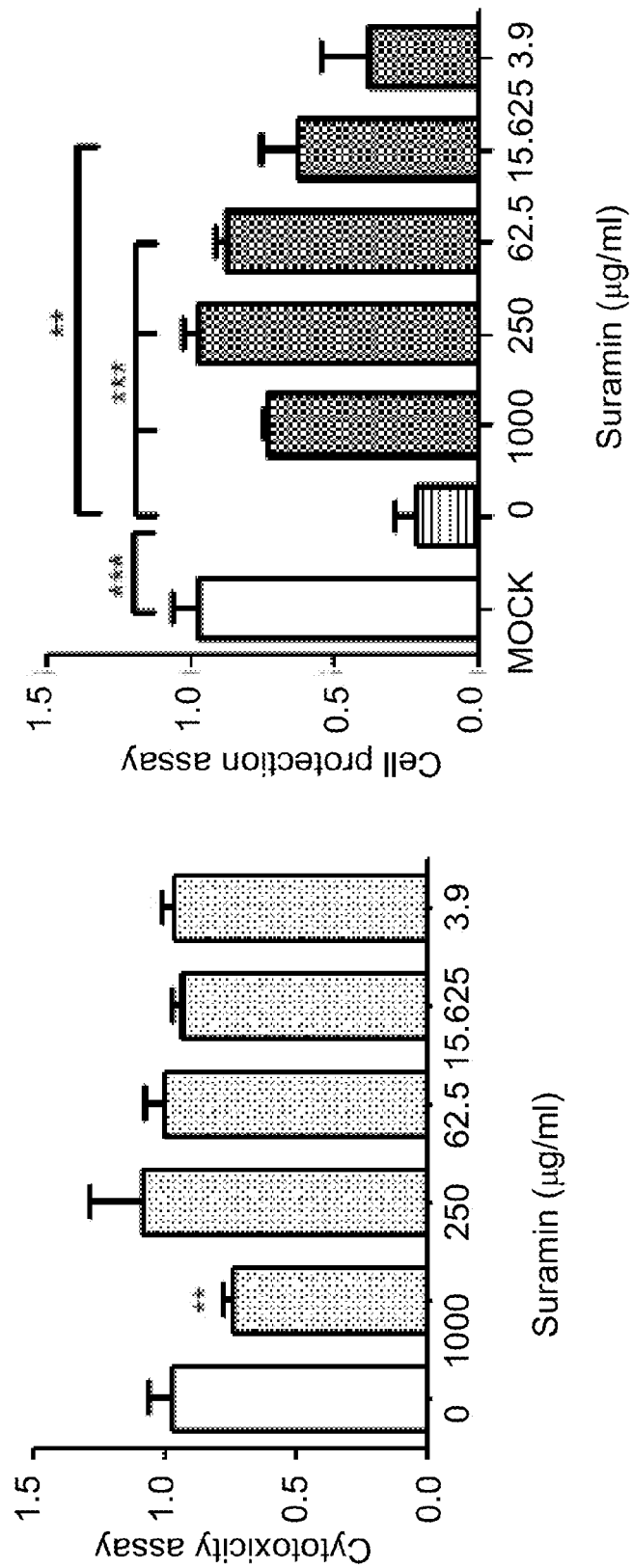
FIG. 18 provide two histograms illustrating the results cytotoxicity assay and the cell protection assay of suramin against CHIKV infection according to Example 10 of the present disclosure.

The results, as provided in FIG. 18, indicate that the addition of suramin protects BHK-21 cells from the cytopathic effect of CHIKV infection At a dose of 1,000 µg/ml, suramin exhibits minimal cytotoxicity (FIG. 18; left panel). Moreover, suramin significantly protects the cells from CHIKV infection at concentrations of 15.6-1,000 µg/ml.

In sum, results from the foregoing working examples establish that suramin not only inhibits the cell fusion in cells infected by the present recombinant virus, CS-WT, but also inhibit CHIKV infection in vitro. Accordingly, suramin can be used as to treat CHIKV infection in a living subject. Alternatively, suramin can be used to inhibit CHIKV infection in vitro.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for inhibiting the infection or replication of the Chikungunya virus in a host cell in vitro, comprising administering to the host cell an effective amount of suramin.

2. The method of claim 1, wherein the host cell belongs to Sf21 cell line or BHK-21 cell line.

3. The method of claim 1, wherein the effective amount is at least 27.5 µM.

4. The method of claim 3, wherein the effective amount is 27.5 µM to 1,750 µM.

5. The method of claim 4, wherein the effective amount is 50 µM to 350 µM.

* * * * *